(12) United States Patent
Sowinski et al.

(10) Patent No.: US 7,655,035 B2
(45) Date of Patent: Feb. 2, 2010

(54) VARIABLE LAMINATION OF VASCULAR GRAFT

(75) Inventors: Krzysztof Sowinski, Wallington, NJ (US); Jamie Henderson, Oakland, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 148 days.

(21) Appl. No.: 11/243,821

(22) Filed: Oct. 5, 2005

(65) Prior Publication Data

US 2007/0078512 A1    Apr. 5, 2007

(51) Int. Cl.
 *A61F 2/06* (2006.01)
(52) U.S. Cl. ............... 623/1.3; 623/1.49; 623/1.39; 623/1.32; 623/1.28
(58) Field of Classification Search ........... 623/1.13, 623/1.23, 1.25, 1.27, 1.28–1.3, 1.32, 1.39, 623/1.4, 1.44, 1.49, 1.5–1.54
See application file for complete search history.

(56) References Cited

U.S. PATENT DOCUMENTS

| | | | |
|---|---|---|---|
| 4,503,569 A | 3/1985 | Dotter | |
| 4,580,568 A | 4/1986 | Gianturco | |
| 4,732,152 A | 3/1988 | Wallsten et al. | |
| 4,733,665 A | 3/1988 | Palmaz | |
| 4,856,516 A | 8/1989 | Hillstead | |
| 4,886,062 A | 12/1989 | Wiktor | |
| 5,718,973 A | 2/1998 | Lewis et al. | |
| 5,749,880 A * | 5/1998 | Banas et al. | 606/198 |
| 6,001,125 A | 12/1999 | Golds et al. | |
| 6,036,724 A | 3/2000 | Lentz et al. | |
| 6,156,064 A | 12/2000 | Chouinard | |
| 6,245,099 B1 | 6/2001 | Edwin et al. | |
| 6,428,569 B1 | 8/2002 | Brown | |
| 6,440,166 B1 | 8/2002 | Kolluri | |
| 6,451,047 B2 | 9/2002 | McCrea et al. | |
| 6,695,833 B1 | 2/2004 | Frantzen | |
| 6,709,455 B1 | 3/2004 | Chouinard | |
| 6,776,604 B1 | 8/2004 | Chobotov et al. | |
| 7,393,359 B2 * | 7/2008 | Verin et al. | 623/1.44 |

(Continued)

FOREIGN PATENT DOCUMENTS

EP     0 137 605     4/1985

(Continued)

OTHER PUBLICATIONS

PCT Notification of Transmittal of the International Search Report and the Written Opinion of the International Searching Authority, or the Declaration for Internatioanl Application No. PCT/US2006/036841, Jan. 4, 2007 (2 pages).

(Continued)

*Primary Examiner*—William H. Matthews
*Assistant Examiner*—Suba Ganesan
(74) *Attorney, Agent, or Firm*—Vidas, Arrett & Steinkraus

(57) ABSTRACT

The vascular graft includes a conduit structure having outer and inner wall surfaces. The conduit structure includes a longitudinal central portion having a flexibility. The conduit structure further includes a pair of longitudinal intermediate portions each of which are integral with the central portion and located longitudinally such that the central portion is between the intermediate portions. The intermediate portions each have a flexibility which is less than the flexibility of the central portion.

21 Claims, 7 Drawing Sheets

U.S. PATENT DOCUMENTS

| | | |
|---|---|---|
| 2001/0023370 A1 | 9/2001 | Smith et al. |
| 2002/0035396 A1 | 3/2002 | Heath |
| 2004/0162604 A1 | 8/2004 | Sowinski et al. |
| 2005/0055045 A1 | 3/2005 | DeVries et al. |

FOREIGN PATENT DOCUMENTS

| | | |
|---|---|---|
| WO | WO 97/27820 | 8/1997 |
| WO | WO 00/18328 | 4/2000 |
| WO | WO 0071057 | 11/2000 |
| WO | WO 01/00112 | 1/2001 |

OTHER PUBLICATIONS

PCT International Search Report for International Application No. PCT/US2006/036841, Jan. 4, 2007 (4 pages).

PCT Written Opinion of the International Searching Authority for International Application No. PCT/US2006/036841, Jan. 4, 2007 (5 pages).

* cited by examiner $L_3 > L_1$
$L_4 < L_2$

VARIABLE LAMINATION OF VASCULAR GRAFT

FIELD OF THE INVENTION

The present invention relates generally to a vascular graft formed of polytetrafluoroethylene (PTFE). More specifically, the present invention relates to such a vascular graft having longitudinal portions distributed along the graft where the flexibilities of abutting pairs of longitudinal portions differ from one another. Also, the present invention relates to a mandrel and method for making the vascular graft.

BACKGROUND OF THE INVENTION

It is well known to use extruded tubes of polytetrafluoroethylene (PTFE) as implantable intraluminal prostheses, particularly vascular grafts. PTFE is particularly suitable as an implantable prosthesis as it exhibits superior biocompatibility. PTFE tubes may be used as vascular grafts in the replacement or repair of a blood vessel as PTFE exhibits low thrombogenicity. In vascular applications, the grafts are manufactured from expanded polytetrafluoroethylene (ePTFE) tubes. These tubes have a microporous structure which allows natural tissue ingrowth and cell endothelization once implanted in the vascular system. This contributes to long term healing and patency of the graft. Grafts formed of ePTFE have a fibrous state which is defined by the interspaced nodes interconnected by elongated fibrils.

One disadvantage of current thin-walled or thicker-walled implantable ePTFE tubes is their tendency to kink when subjected to bending forces or concentrated external radial forces. Kinking and luminal constriction can occur during or subsequent to implantation. Such kinking is normally undesirable and poses a risk to the patient.

Accordingly, in applications where kinking is likely, vascular grafts have an additional support structure to prevent kinking. Typically, external support structures, such as helical coils, are bonded around the outer surface of the ePTFE tube. Alternatively, individual rings may be bonded to the outer surface of the ePTFE by injection molding.

Such additional support structures have several disadvantages. For example, the additional support structures are normally bonded to the outer surface of the ePTFE tube thereby increasing the outer diameter of the graft in the regions of the support structures. As a result, implantation of the graft can become more difficult. For example, when tunneling through tissue is required to implant the graft, such as in vascular access applications, a larger cross-sectional tunnel area is required to allow for insertion of the graft.

Another disadvantage of grafts having added support structures is that they are often made from materials which are different from the material of the graft wall and require added processing steps such as heat bonding or additional materials such as adhesive to adhere the support structure to the graft. Differential shrinkage or expansion of the external support structure relative to the ePTFE tube can cause the bond to weaken and/or the graft to twist significantly. Separation of the support structure from the graft is obviously undesirable. Additionally, twisting will normally distort the printed linear guideline which typically runs the length of the ePTFE tube and is used by practitioners to determine proper graft disposition to prevent implantation in a twisted configuration. Such distortion may result in the normally longitudinally linear guideline becoming helical or some other non-linear shape prior to implantation of the vascular graft in the patient, thereby defeating the purpose of the guideline.

Other ePTFE grafts have included external polymeric ribs which provide radial support to the lumen, but increase the outer diameter and wall thickness of the graft.

Thus, there is a need for PTFE tubes which are kink resistant without added support structures such as coils or rings and which do not increase the tube outer diameter.

SUMMARY OF THE INVENTION

The vascular graft of the present invention includes a conduit structure having outer and inner wall surfaces. The conduit structure includes a longitudinal central portion having a flexibility. The conduit structure further includes a pair of longitudinal intermediate portions each of which are integral with the central portion and located longitudinally such that the central portion is between the intermediate portions. The intermediate portions each have a flexibility which is less than the flexibility of the central portion.

The vascular graft has several advantages. The greater flexibility of the central portion provides for greater bending thereof without kinking which, in turn, provides for greater bending of the conduit structure without kinking. The reduced flexibilities of the intermediate portions provide structural support to the conduit structure. Such structural support is beneficial for thin-walled and thicker-walled PTFE tube, and is especially beneficial for thin-walled PTFE tube. Also, the outer diameter of the central and intermediate portions is not significantly greater than the outer diameter of a conventional PTFE tube.

Further, the integral relation of the central and intermediate portions to the conduit structure, i.e., the portions are part of the conduit structure which has a uniform material, normally eliminates the possibility of differential shrinkage or expansion of the portions relative to the other portions of the conduit structure. This greatly reduces the possibility of twisting of the conduit structure, and the associated distortion of the guideline prior to insertion of the graft into the patient, which may result from such twisting. The integral relation of the central and intermediate portions to the conduit structure normally eliminates the possibility of the portions becoming detached from the conduit structure.

A mandrel and method for making the vascular graft of the present invention facilitates the formation of the central and intermediate portions of the conduit structure.

These and other features of the invention will be more fully understood from the following description of specific embodiments of the invention taken together with the accompanying drawings.

BRIEF DESCRIPTION OF THE DRAWINGS

In the drawings.

Corresponding reference characters indicate corresponding parts throughout the several views of the drawings.

DETAILED DESCRIPTION OF THE INVENTION

Figure 1:
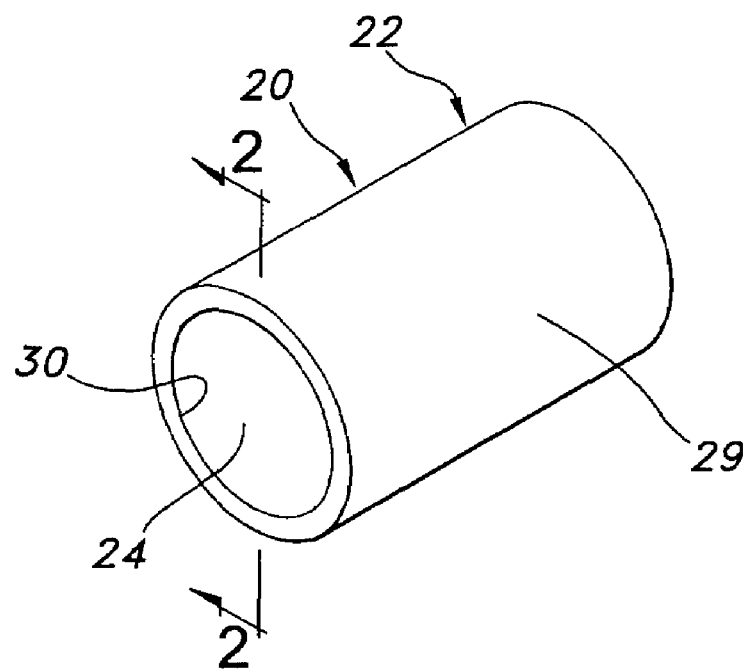
FIG. 1 is a perspective view of the variably laminated vascular graft of the present invention, the graft being shown as having a conduit structure including central and intermediate portions.
Figure 2:
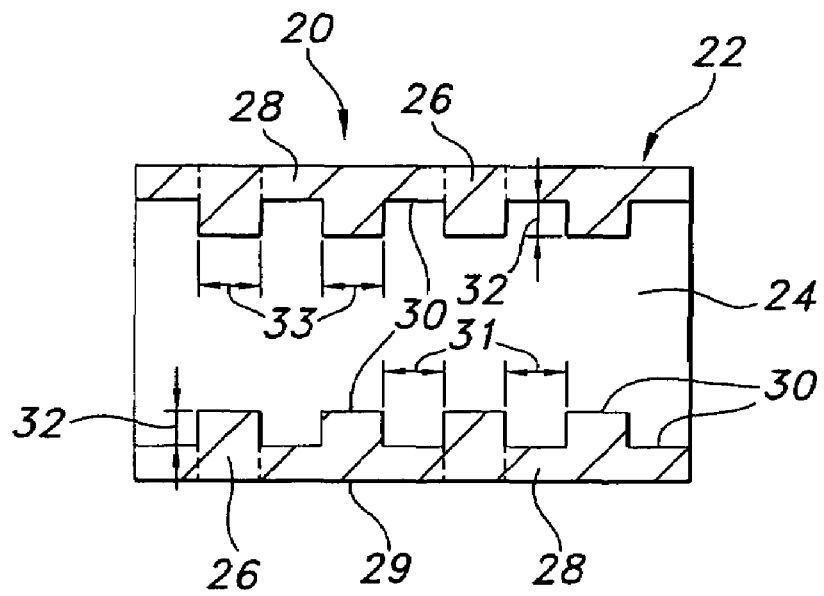
FIG. 2 is a longitudinal cross-sectional view of the vascular graft of FIG. 1 in the plane indicated by line 2-2 of FIG. 1.

Referring to the drawings and more particularly to FIGS. 1 and 2, a vascular graft 20 is shown for implantation within a body. The vascular graft 20 includes a conduit structure 22 formed of expanded PTFE material. The conduit structure 22 is elongate and has lumen 24 for carrying fluids, such as blood. The central and intermediate portions 26, 28 each have a cross-section which is annular such that the conduit structure 22 has a cross-section which is annular. In alternative embodiments, the cross-sections of the central and intermediate portions 26, 28 and conduit structure 22 may be non-annular, such as by being rectangular.

The conduit structure 22 has longitudinal central and intermediate portions 26, 28 which are in integral and alternating relation to one another. The longitudinal central portions 26 have respective radial or transverse wall thicknesses which are greater than the respective radial or transverse wall thicknesses of the longitudinal intermediate portions 28. The wall thicknesses of the central and intermediate portions 26, 28 are bounded by the outer and inner wall surfaces 29, 30 of the conduit structure 22.

The extensions of the central portions 26 which constitute the inner wall surface 30 are separated from the immediately preceding or following central portions by respective longitudinal dimensions 31 which are the same. In alternative embodiments of the conduit structure 22, the longitudinal dimensions which separate the immediately preceding or following central portions may be different. The extensions of the central portions 26 each have a transverse dimension 32 which is the same for all of the central portions. The extensions of the central portions 26 each have a longitudinal dimension 33 which is the same for all of the extensions. In alternative embodiments of the conduit structure 22, the longitudinal and transverse dimensions of the extensions may be different. In further alternative embodiments of the conduit structure 22, the shapes of the extensions may be different.

The conduit structure 22 is required to have at least one of the longitudinal central portions 26 and at least two of the longitudinal intermediate portions 28. In such a conduit structure 22, the central portion 26 would be located between the intermediate portions 28. The longitudinal intermediate portions 28 may adjoin the longitudinal central portion 26 or be longitudinally spaced apart from it. The conduit structure 22 may have more than one longitudinal central portion 26, as shown in FIG. 2, and such central portions may have the alternating relation to the longitudinal intermediate portions 28 shown in FIG. 2. The numbers of longitudinal central and intermediate portions 26, 28 may be different in various embodiments of the conduit structure 22.

Figure 3:
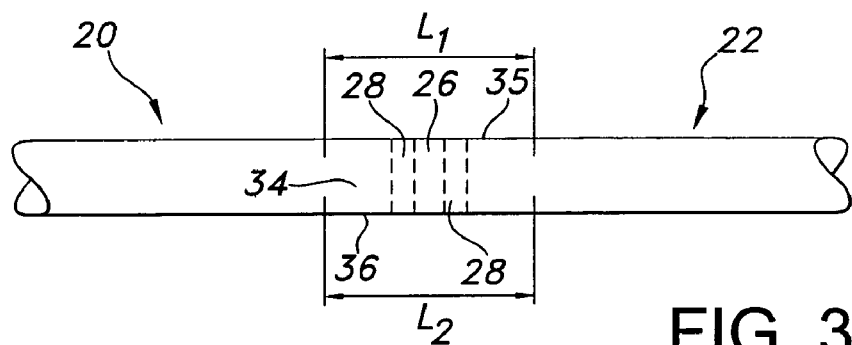
FIG. 3 is a schematic external view of the vascular graft of FIG. 1, the graft being shown as being straight.

The difference in the wall thicknesses of the central and intermediate portions 26, 28 results from the intermediate portions being more compressed, in the radial direction, relative to the central portions. The reduced compression of the central portions 26 relative to the intermediate portions 28 results in the central portions having a greater flexibility relative to the flexibility of the intermediate portions. This provides the conduit structure 22 with greater bending flexibility which allows the conduit structure to be bent into a curved configuration, as illustrated schematically in FIGS. 3 and 4. FIG. 3 shows the conduit structure 22 of FIG. 1 in a straight configuration. The conduit structure 22 shown in FIG. 3 has a longitudinal portion 34 which includes at least one of the central portions 26. The longitudinal portion 34 includes outer and inner walls 35, 36 which have respective longitudinal lengths designated by $L_1$ and $L_2$. The ends of the longitudinal portion 34 are transverse to the longitudinal axis of the conduit structure 22, as shown in FIG. 3.

Figure 4:
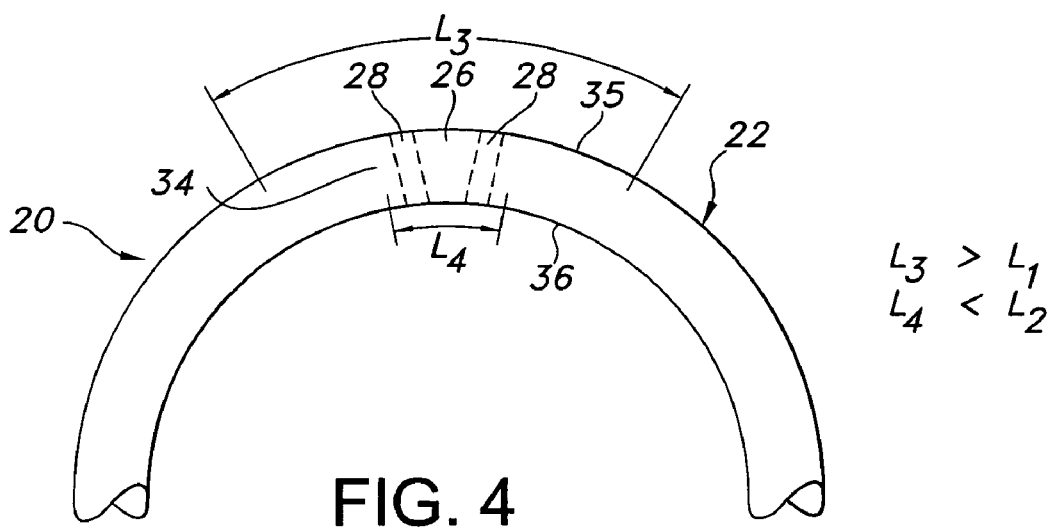
FIG. 4 is a schematic external view of the vascular graft of FIG. 3, the graft being shown as being bent.

FIG. 4 shows the conduit structure 22 of FIG. 3 being bent into a curved configuration. The longitudinal lengths of the outer and inner walls 35, 36, which have a curved configuration, are designated by $L_3$ and $L_4$. As shown in FIG. 4, the lengths $L_3$ and $L_4$ differ from one another as a result of the curvature of the longitudinal portion 34. Also, the length $L_3$ is greater than the length $L_1$ of the longitudinal portion 34 in the straight configuration of FIG. 3. The length $L_4$ is less than the length $L_2$ of the longitudinal portion 34 in the straight configuration of FIG. 3. These comparisons show that longitudinal portion 34 is deformed when it is bent from the straight configuration of FIG. 3 to the curved configuration of FIG. 4. During this deformation, the longitudinal portion 34 advantageously retains the curved configuration shown in FIG. 4 and does not kink or fold, in contrast to the vascular graft 37 shown in FIG. 5.

Figure 5:
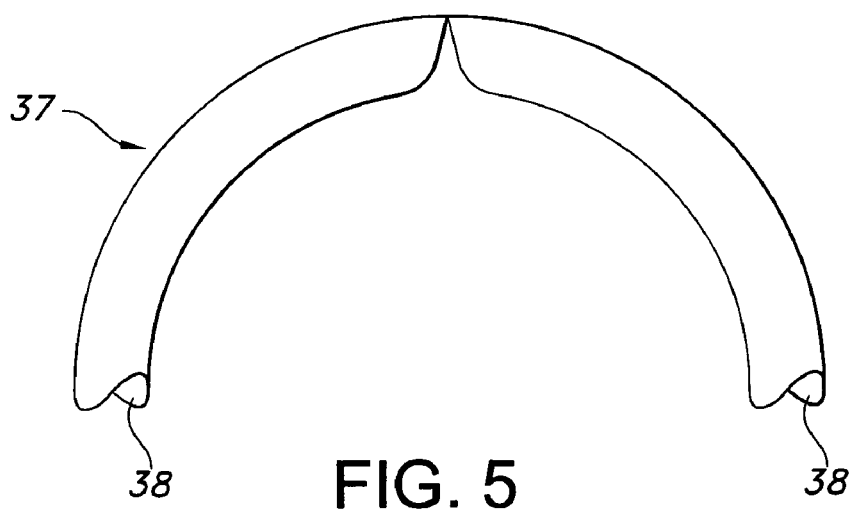
FIG. 5 is a schematic external view of a conventional vascular graft, the graft being shown as bent to the same degree as the graft of FIG. 4.

FIG. 5 shows a vascular graft 37 of a conventional type which may kink or fold when it is bent to the same degree as the vascular graft 20 shown in FIG. 4. The kinking shown in FIG. 5 is undesirable for several reasons including the resulting reduction in the cross-sectional area of the lumen 38. The kink in the inner wall 40 may extend into the lumen 38 resulting in the partial obstruction thereof or, as shown in FIG. 5, extend to the outer wall 42 which may result in the complete obstruction of the lumen. Another negative effect of the kinking is the weakening of the inner wall 40 which may result from the folding thereof. Further disadvantages include the possible kinking of the outer wall 42 which may result from it being impinged against by the inner wall 40. Alternatively, kinking of the outer wall 42 may result from bending stresses therein which correspond to the bending stresses which produce the kinking of the inner wall 40.

The maintenance of the curved configuration of the longitudinal portion 34 during the bending thereof shown in FIG.

4, as compared to the kinking shown in FIG. 5, is provided by the one or more central portions 26 within the longitudinal portion 34. This bending flexibility provided by the central portions 26 allows the conduit structure 22 to be deflected to a degree which may cause kinking or folding of a more conventional tube formed of PTFE, such as is illustrated in FIG. 5.

The conduit structure 22 has an outer diameter, or outer transverse dimension, which is constant along the conduit structure. Accordingly, the outer diameters of the central and intermediate portions 26, 28 are the same. To provide for the larger wall thickness of the central portions 26 relative to the intermediate portions 28, the inner diameter, or inner transverse dimension, of the central portions 26 is less than the inner diameter, or inner transverse dimension, of the intermediate portions 28, as shown in FIG. 2.

The different wall thicknesses of the central and intermediate portions 26, 28 results from the greater compression of intermediate portions 28 relative to the central portions 26. This difference in compression also provides for the density of the central portions 26 to be less than the density of the intermediate portions 28, and the density to be inversely related to the wall thickness. The difference in compression of the central and intermediate portions 26, 28 also provides for the porosity of the central portions 26 to be greater than the porosity of the intermediate portions 28, and the porosity to be positively related to the wall thickness.

Figure 6:
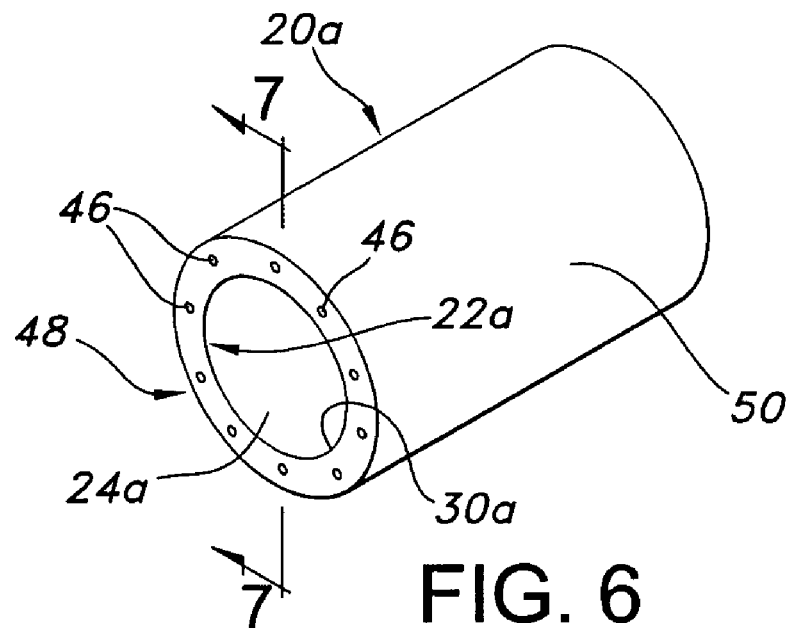
FIG. 6 is a perspective view of the of an alternative embodiment of the vascular graft of FIG. 1, the alternative embodiment being shown as having a stent structure between outer and inner conduit structures.
Figure 7:
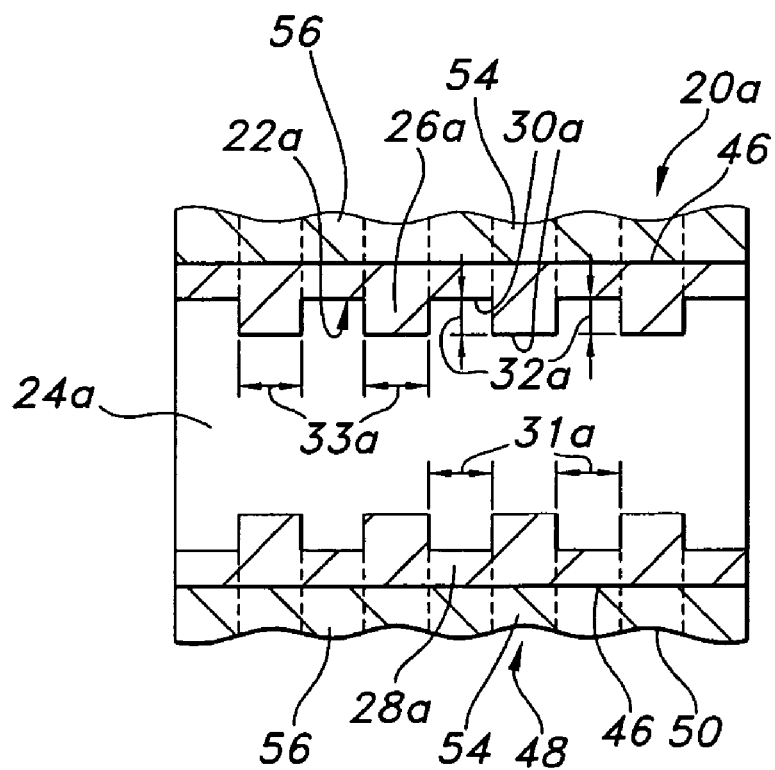
FIG. 7 is a longitudinal cross-sectional view of the vascular graft of FIG. 6 in the plane indicated by line 7-7 of FIG. 6.

The conduit structure 22 may constitute an inner conduit structure 22a of a vascular graft 20a which also includes a stent structure 46 and an outer conduit structure 48, as shown in FIGS. 6 and 7. The vascular graft 20a, and the parts thereof such as the inner conduit structure 22a, which correspond to the vascular graft 20 have the same reference numeral as in FIGS. 1 and 2 with the addition of the suffix "a". The inner and outer conduit structures 22a, 48 and stent structure 46 are laminated to one another as shown in FIGS. 6 and 7.

Figure 8:
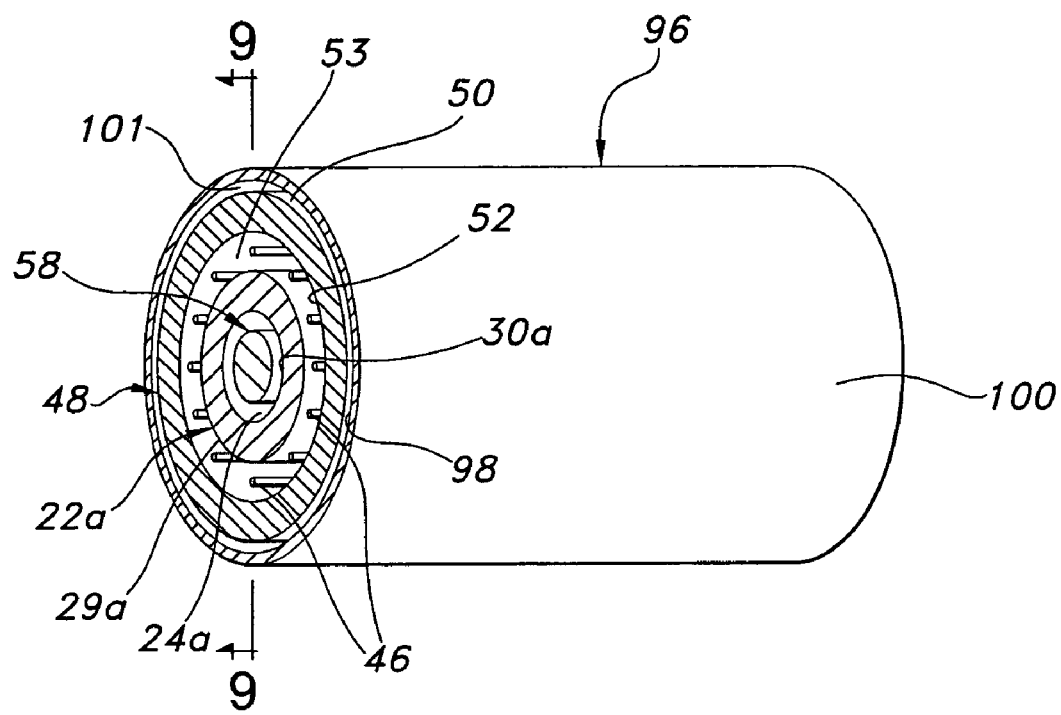
FIG. 8 is a perspective view of the vascular graft of FIG. 6 showing the assembly of the cover structure, outer conduit structure, stent structure, inner conduit structure, and mandrel, the assembly being shown before the lamination of the outer conduit structure, stent structure and inner conduit structure.
Figure 9:
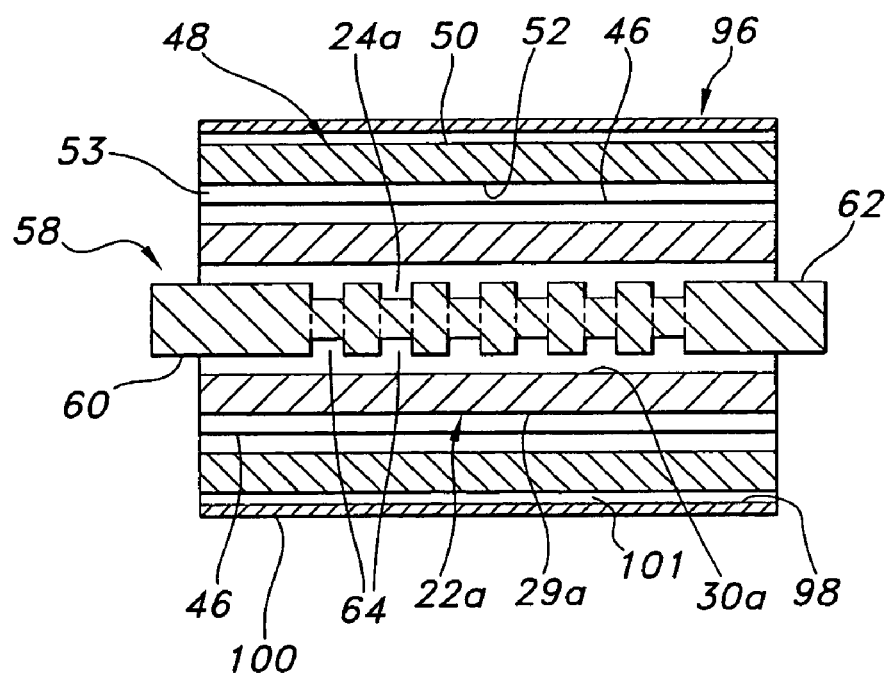
FIG. 9 is a longitudinal cross-sectional view of the vascular graft of FIG. 8 in the plane indicated by line 9-9 of FIG. 8.

The vascular graft 20a is made by arranging the stent structure 46 in close or abutting relation to the outer wall surface 29a of the inner conduit structure 22a, as shown in FIGS. 8 and 9. The stent structure 46 may be constituted by a winding zig-zag stent, laser cut tube stent, or braided stent. Also, the stent structure 46 may be formed of materials such as nitinol, elgiloy, stainless steel or cobalt chromium, including NP35N. Additionally, the stent structure 46 may be formed of materials such as stainless steel, platinum, gold, titanium and other biocompatible metals, as well as polymeric stents. Also, the stent structure 46 may be formed of materials including cobalt-based alloy such as Elgiloy, platinum, gold, titanium, tantalum, niobium, and combinations thereof and other biocompatible materials, as well as polymers. Additionally, the stent structure 46 may include structural members which have an inner core formed of tantalum gold, platinum, iridium, or a combination thereof, and an outer cladding of nitinol to provide composite members for improved radio-opacity or visibility. Examples of such composite members are disclosed in U.S. Patent Application Publication 2002/0035396, the entire contents of which are hereby incorporated by reference herein.

The stent structure 46 may have various embodiments. For example, the stent structure 46 may be self-expanding or expandable by a balloon. The stent structure 46 may include one or more coiled stainless steel springs, helically wound coil springs including a heat-sensitive material, or expanding stainless steel stents formed of stainless steel wire in a zig-zag pattern. The stent structure 46 may be capable of radially contracting or expanding, such as by radial or circumferential distension or deformation. Self-expanding stents include stents which mechanically urge the stent to radially expand, and stents which expand at one or more specific temperatures as a result of the memory properties of the stent material for a specific configuration. Nitinol is a material which may be included in the stent structure 46 for providing radial expansion thereof both by mechanical urging, or by the memory properties of the nitinol based on one or more specific temperatures. The stent structure 46 may include one or more of the stents disclosed in U.S. Pat. Nos. 4,503,569, 4,733,665, 4,856,516, 4,580,568, 4,732,152, and 4,886,062, the entire contents of each of which are hereby incorporated by reference herein.

The outer conduit structure 48 has an outer wall surface 50 and, before the lamination of the outer conduit structure 48 to the stent and inner conduit structures 46, 22a, an inner wall surface 52, as shown in FIGS. 8 and 9. The outer conduit structure 48 is elongate and, before the lamination, has a lumen 53 which is bounded transversely by the inner wall surface 52. The outer conduit structure 48 is arranged in coaxial relation to the inner conduit structure 22a such that the stent and inner conduit structures 46, 22a are within the outer conduit structure. Before the lamination, the stent structure 46 is in close or abutting relation to the inner wall surface 52 of the outer conduit structure 48, as shown in FIGS. 8 and 9.

The outer conduit structure 48 is formed of expanded PTFE material. Before the lamination, the cross-sectional shape of the outer conduit structure is preferably the same as the cross-sectional shape of the inner conduit structure which is annular, as shown in FIGS. 6 and 7. It is possible for the cross-sectional shape of the outer conduit structure 48 to differ from the cross-sectional shape of the inner conduit structure 22a before the lamination of the structures to one another. After the lamination, the cross-sectional shapes of the inner and outer conduit structures 22a, 48 are typically the same, as shown in FIGS. 6 and 7.

Compressing the outer and inner conduit structures 48, 22a against the mandrel 58 results in the formation in the outer conduit structure 48 of longitudinal central and intermediate portions 54, 56 which are integral and in alternating relation to one another. The outer conduit structure 48 is required to have at least one of the longitudinal central portions 54 and at least two of the longitudinal intermediate portions 56. In such a conduit structure 48, the central portion 54 would be located between the intermediate portions 56. The reduced compression of the central portions 54 relative to the intermediate portions 56 results in the central portions 54 having a greater flexibility relative to the flexibility of the intermediate portions 56. This provides the outer conduit structure 48 with greater bending flexibility in a manner which corresponds to the greater flexibility provided by the central portions 26, as illustrated in FIGS. 3 to 5.

In the vascular graft 20a shown in FIGS. 6 and 7, the flexibilities of the central portions 26a, 54 are equal, and the flexibilities of the intermediate portions 28a, 56 are equal. In alternative embodiments, it is possible for the flexibilities of the central portions 26a, 54 to be different, and for the flexibilities of the intermediate portions 28a, 56 to be different, provided that the flexibilities of the central portions 26a, 54 are greater than the flexibilities of the intermediate portions 28a, 56.

Figure 13:
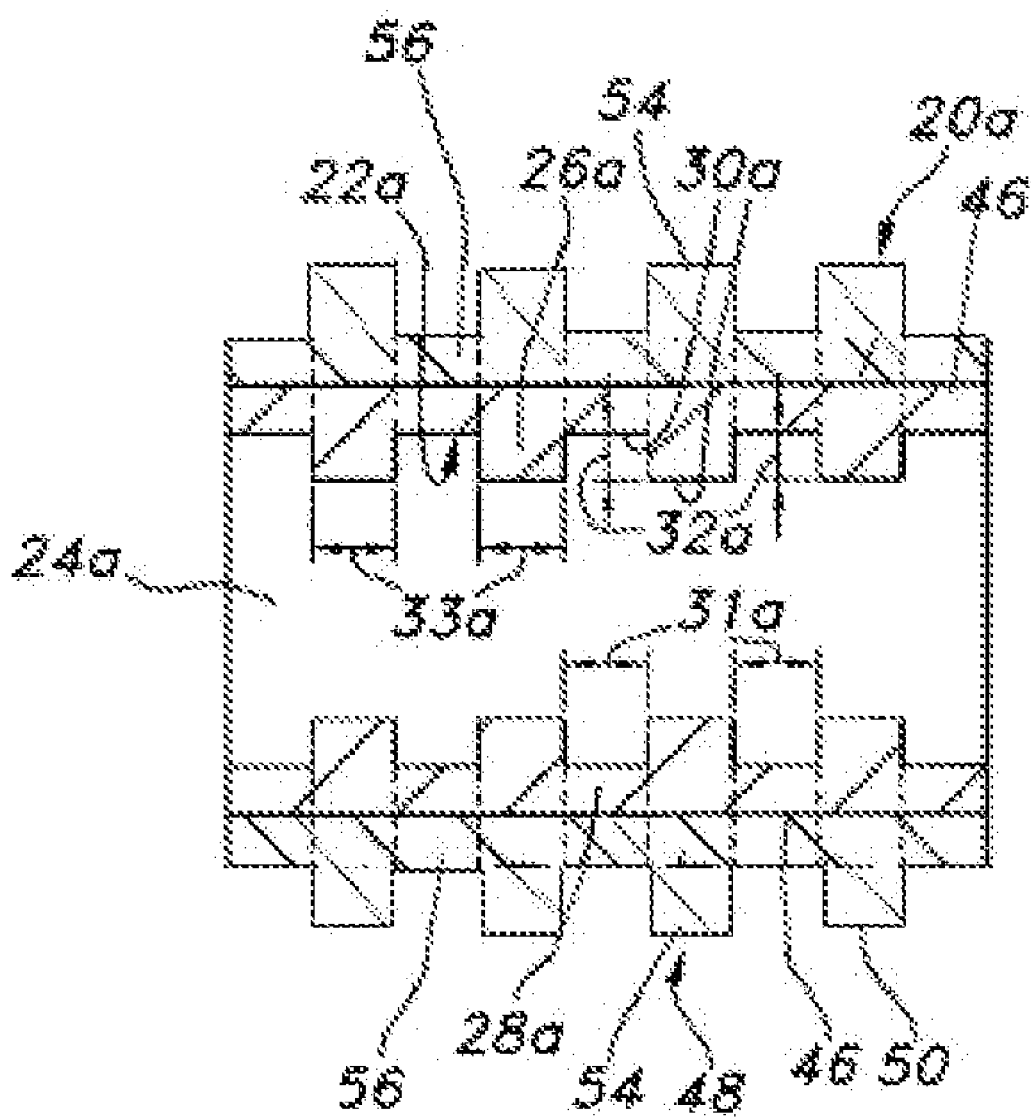
FIG. 13 is a schematic view of the longitudinal cross-section of the outer conduit structure and stent assembly of another embodiment of the invention taken in the plane indicated by line 7-7 of FIG. 6.

The central and intermediate portions 54, 56 of the outer conduit structure 48 each correspond to a respective central or intermediate portion 26a, 28a of the inner conduit structure 22a, as shown in FIG. 7. The central portions 26a, 54 have approximately the same longitudinal position and the intermediate portions 28a, 56 have approximately the same longitudinal position relative to the vascular graft 20a, as shown in FIG. 7. The central portion 54 of the outer conduit structure may, optionally, be thicker than the intermediate portion of the outer conduit structure 56, as shown in FIG. 13. In alternative embodiments, it is possible for the inner or outer conduit structures 22a, 48 to have additional central and intermediate portions which extend longitudinally beyond the central and intermediate portions 26a, 54, 28a, and 56 which are in corresponding relation to one another.

The greater compression of intermediate portions 56 relative to the central portions 54 provides for the density of the central portions 54 to be less than the density of the intermediate portions 56, and the density to be inversely related to the wall thickness. The difference in compression of the central and intermediate portions 54, 56 also provides for the porosity of the central portions 54 to be greater than the porosity of the intermediate portions 56, and the porosity to be positively related to the wall thickness.

The lamination of the inner and outer conduit structures 22a, 48 results in the fusing together of the outer and inner wall surfaces 29, 52. Before the fusing, the stent structure 46 is positioned between the inner and outer conduit structures 22a, 48, as shown in FIGS. 8 and 9. Consequently, the fusing results in portions of one or both of the outer and inner wall surfaces 29, 52 extending between the members of the stent structure 46 for locking thereof between the conduit structures, as shown in FIGS. 6 and 7.

The lamination and compression of the inner and outer conduit structures 22a, 48 results in the vascular graft 20a having a radial or transverse wall thickness which varies depending upon the longitudinal position on the vascular graft 20a. The wall thickness of the vascular graft 20a is larger for the portions thereof which contain the central portions 26a, 54. eas compared to the wall thickness of the portions of the vascular graft 20a which contain the intermediate portions 28a, 56, as shown in FIG. 7. This is a consequence of the greater compression of the intermediate portions 28a, 56 as compared to the central portions 26a, 54. The intermediate portions 28a, 56 may resist compression to a greater degree than the central portions 26a, 54 such that the outer wall 50 which is constituted by the central portions 54 is displaced transversely inward to a greater degree as compared to the outer wall 50 which is constituted by the intermediate portions 56, as shown in FIG. 7.

The lamination and compression of the inner and outer conduit structures 22a, 48 may result in the blending of the transversely adjoining central portions 26a, 54 thereof. Also, the lamination and compression of the inner and outer conduit structures 22a, 48 may result in blending of the transversely adjoining intermediate portions 28a, 56 thereof. Additionally, the lamination and compression of the inner and outer conduit structures 22a, 48 may result in the blending of the longitudinally adjoining central and intermediate portions 26a, 28a of the inner conduit structure 22a. Further, the lamination and compression of the inner and outer conduit structures 22a, 48 may result in the blending of the longitudinally adjoining central and intermediate portions 54, 56 of the outer conduit structure.

The inner and outer conduit structures 22a, 48 and stent structure 46, in combination after the lamination, have a cross-section which is annular. This is provided by the central and intermediate portions 26a, 28a of the inner conduit structure 22a each having a cross-section in which the inner wall surface 30a thereof is circular. The annular cross-section is further provided by the central and intermediate portions 54, 56 of the outer conduit structure 48 each having a cross-section in which the outer wall surface 50 thereof is circular.

The inner surfaces of the central and intermediate portions 54, 56 which are contained in the cross-sections thereof are circular. Also, the outer surfaces of the central and intermediate portions 26a, 28a which are contained in the cross-sections thereof are circular. In alternative embodiments, it is possible for the inner surfaces of the central and intermediate portions 54, 56 and the outer surfaces of the central and intermediate portions 26a, 28a which are contained in the respective cross-sections thereof to be non-circular while the inner and outer conduit structures 22a, 48 and stent structure 46, in combination after the lamination, have a cross-section which is annular.

The conduit structure 22, inner and outer conduit structures 22a, 48, and stent structure 46 may be treated with anti-thrombogenic agents (such as heparin, heparin derivatives, urokinase, and PPack (dextrophenylalanine proline arginine chloromethylketone)), anti-proliferative agents (such as enoxaprin, angiopeptin, or monoclonal antibodies capable of blocking smooth muscle cell proliferation, hirudin, and acetylsalicylic acid), anti-inflammatory agents (such as dexamethasone, prednisolone, corticosterone, budesonide, estrogen, sulfasalazine, and mesalamine), antineoplastic/antiproliferative/anti-miotic agents (such as paclitaxel, 5-fluorouracil, cisplatin, vinblastine, vincristine, epothilones, endostatin, angiostatin and thymidine kinase inhibitors), anesthetic agents (such as lidocaine, bupivacaine, and ropivacaine), anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick anti-platelet peptides), vascular cell growth promotors (such as growth factor inhibitors, growth factor receptor antagonists, transcriptional activators, and translational promotors), vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin), cholesterol-lowering agents, vasodilating agents, and agents which interfere with endogenous vascoactive mechanisms.

The inner and outer conduit structures 22a, 48, and conduit structure 22 are preferably formed of ePTFE. Alternatively, or in combination with ePTFE, the inner and outer conduit structures 22a, 48, and conduit structure 22 may be formed of biocompatible materials, such as polymers which may include fillers such as metals, carbon fibers, glass fibers or ceramics. Such polymers may include olefin polymers, polyethylene, polypropylene, polyvinyl chloride, polytetrafluoroethylene which is not expanded, fluorinated ethylene propylene copolymer, polyvinyl acetate, polystyrene, poly (ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk may be included in the inner and outer conduit structures 22a, 48, and conduit structure 22.

Figure 10:
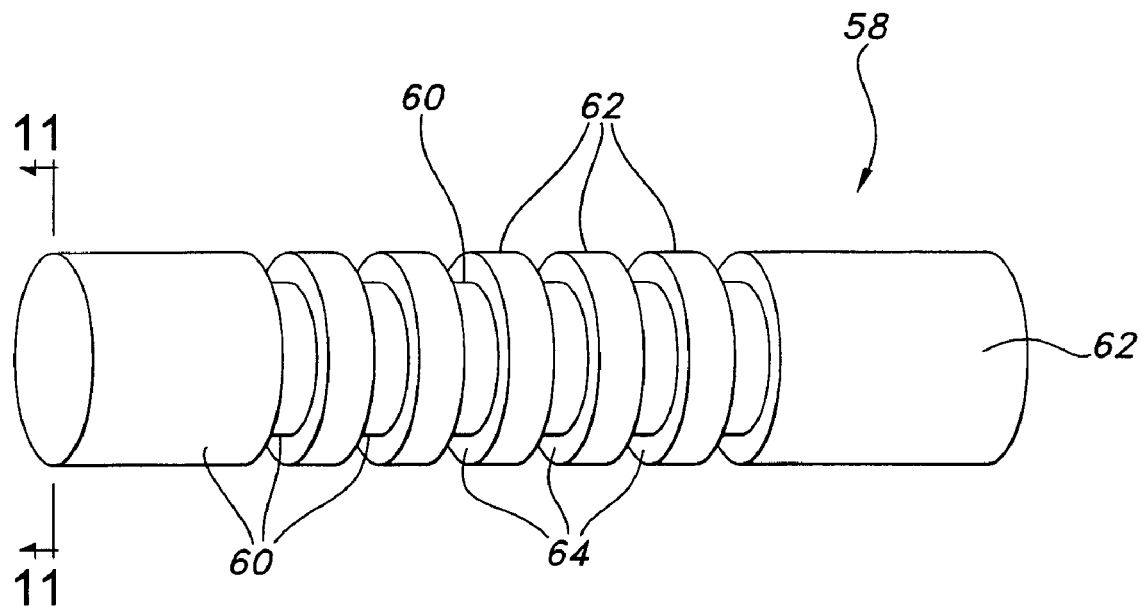
FIG. 10 is a perspective view of a mandrel for making the vascular graft of the present invention, the mandrel being shown as having transverse grooves.
Figure 11:
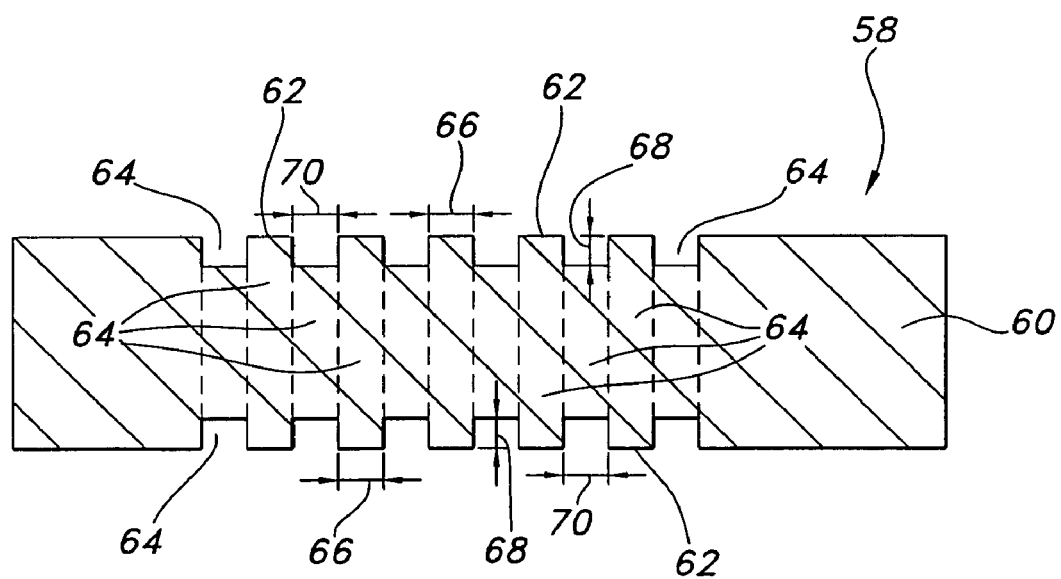
FIG. 11 is a longitudinal cross-sectional view of the mandrel of FIG. 8, the mandrel being shown as having transverse grooves.

A mandrel 58 for making the vascular graft 20, 20a is shown in FIGS. 10 and 11. The mandrel 58 includes an elongate core structure 60 having an outer surface 62 and a circular cross-section. In alternative embodiments, the cross-section of the core structure 60 may be non-circular, such as by being rectangular. The core structure 60 may be formed of various materials, such as stainless steel, glass, ceramic, coated aluminum, or stainless steel with an aluminum press core.

The mandrel 58 has transverse grooves 64 each of which is formed in the core structure 60 such that the grooves each extend inwardly from the outer surface 62. The grooves 64 each extend around the entire periphery of the outer surface 62 and have an annular cross-section. The grooves 64 are separated from the immediately preceding or following grooves by respective longitudinal dimensions 66 which are the same. In alternative embodiments of the mandrel 58, the longitudinal dimensions which separate the immediately preceding or following grooves 64 may be different.

The grooves 64 each have a transverse dimension 68 or depth which is the same for all of the grooves. The grooves 64 each have a longitudinal dimension 70 which is the same for all of the grooves. In alternative embodiments of the mandrel 58, the longitudinal and transverse dimensions of the grooves may be different. In further alternative embodiments of the mandrel 58, the shapes of the grooves may be different. Each groove 64 provides for the formation of the central portions 26 of the conduit structure 22 and central portions 26a, 54 of the inner and outer conduit structures 22a, 48, as described herein below.

In an alternative embodiment, the mandrel 58 may have as few as one groove 64 for making a conduit structure having one central portion, such as the central portions 26, 26a, and two intermediate portions, such as the intermediate portions 28, 28a. Such a conduit structure is described herein above.

Figure 12:
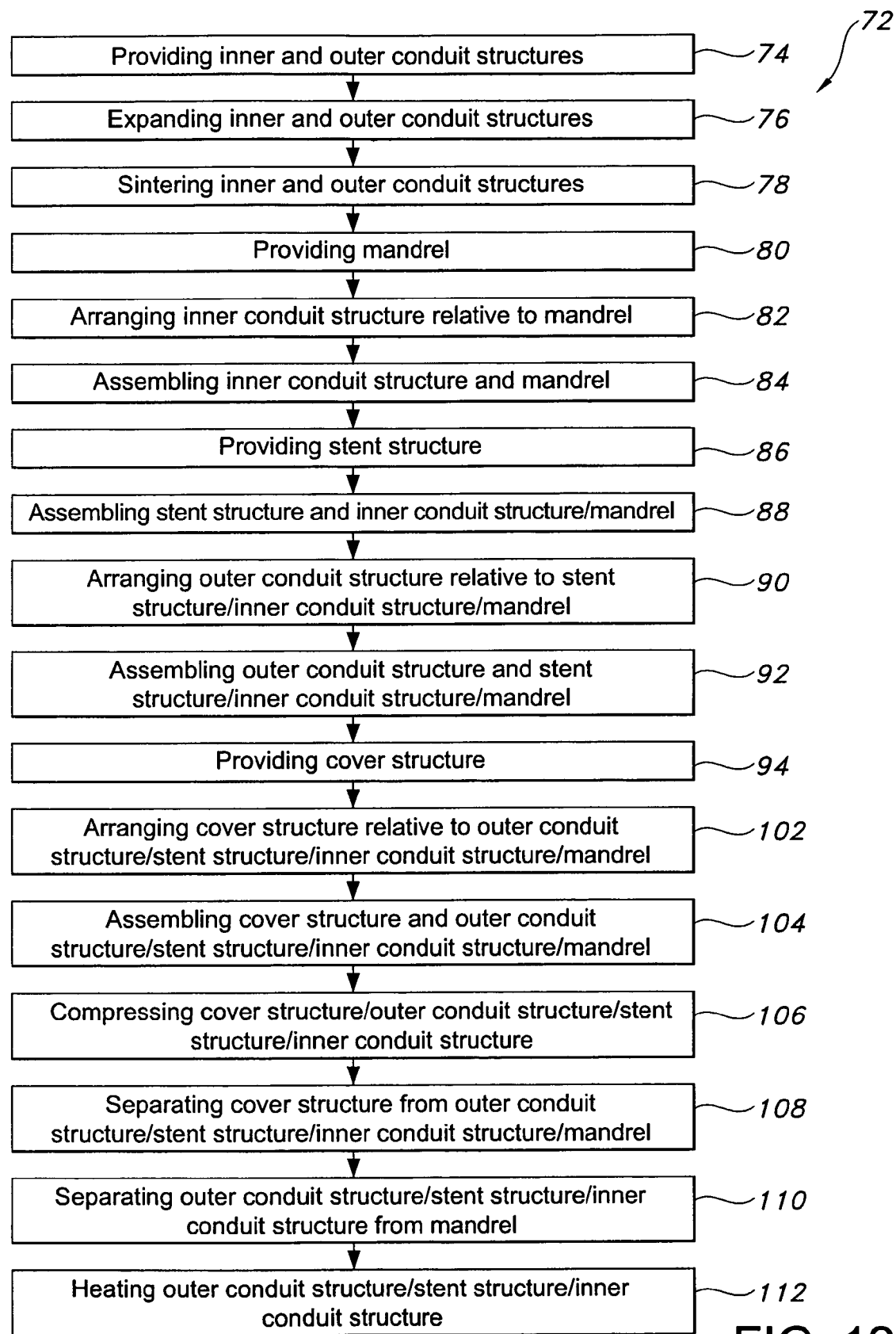
FIG. 12 is a block diagram showing a method for making a vascular graft of the present invention, the method including the steps of compressing the inner conduit structure against the mandrel, and laminating the inner and outer conduit structures.

A method 72 for making the vascular graft 20, 20a is shown in the block diagram of FIG. 12. The method 72 includes providing 74 inner and outer conduit structures each of which is formed of PTFE. The inner and outer conduit structures are longitudinally expanded 76 and then sintered 78. Examples of the inner and outer conduit structures which result from the sintering 78 are the inner and outer conduit structures 22a, 48 shown in FIGS. 8 and 9.

The method 72 further includes providing 80 a mandrel, such as the mandrel 58. The inner conduit structure is arranged 82 in coaxial relation to the core structure of the mandrel. An example of the core structure is the core structure 60 of the mandrel 58. The inner transverse dimension of the inner conduit structure is greater than the outer transverse dimension of the core structure. The core and inner conduit structures are assembled 84 by longitudinally displacing the core structure or inner conduit structure such that the inner wall surface thereof faces the grooves of the mandrel. An example of this arrangement is illustrated in FIGS. 8 and 9 which show the inner wall surface 30a of the inner conduit structure 22a as facing the grooves 64 of the mandrel 58.

The method 72 further includes providing 86 a stent structure, such as the stent structure 46. The stent structure is arranged 88 in close or abutting relation to the outer wall surface of the inner conduit structure. An example of the close or abutting relation is illustrated in FIG. 9 which shows the stent structure 46 in close relation to the inner conduit structure 22a.

The method 72 further includes arranging 90 the outer conduit structure in coaxial relation to the inner conduit structure. The inner transverse dimension of the outer conduit structure is greater than the outer transverse dimension of the inner conduit structure. The outer conduit structure is assembled 92 to the previously assembled inner conduit structure and mandrel by longitudinally displacing the outer conduit structure or previous assembly such that the inner wall surface of the outer conduit structure faces the outer wall surface of the inner conduit structure. An example this arrangement is illustrated in FIGS. 8 and 9 which show the inner wall surface 52 of the outer conduit structure 48 as facing the outer wall surface 29a of the inner conduit structure 22a.

The assembling 92 also provides for the stent structure to be between the inner and outer conduit structures. An example of this arrangement is illustrated in FIGS. 8 and 9 in which the stent structure 46 is shown as between the inner and outer conduit structures 22a, 48.

The method 72 further includes providing 94 a cover structure, such as the cover structure 96 shown in FIGS. 8 and 9. The cover structure has inner and outer wall surfaces, such as the inner and outer wall surfaces 98, 100. The cover structure has a bore which is bounded transversely the inner wall surface. An example of the bore is the bore 101 which is bounded transversely by the inner wall surface 98. The cover structure has an inner transverse dimension which is greater than the outer transverse dimension of the outer conduit structure. The cover structure is formed of silicone material.

The cover structure is arranged 102 in coaxial relation to the outer conduit structure. The cover structure is assembled 104 to the previous assembly of the outer conduit structure, stent structure, inner conduit structure, and mandrel by longitudinally displacing the cover structure or previous assembly such that the inner wall surface of the outer conduit structure faces the outer wall surface of the inner conduit structure. An example this arrangement is illustrated in FIGS. 8 and 9 which show the inner wall surface 52 of the outer conduit structure 48 as facing the outer wall surface 29a of the inner conduit structure 22a.

The method 72 further includes applying gas 106 to the outer wall surface of the cover structure, such as the outer wall surface 100. The gas has a sufficiently elevated pressure to compress 106 the cover structure such that the inner wall surface thereof is forced inwardly into contact with the outer wall surface of the outer conduit structure to compress the outer conduit structure. The compression 106 of the outer conduit structure forces the inner wall surface thereof into contact with the stent structure and outer wall surface of the inner conduit structure to compress 106 the inner conduit structure. The compression 106 of the inner conduit structure forces portions thereof into the grooves of the mandrel and forces the portions of the inner conduit structure between the grooves against the outer surface of the core structure. Additionally, the compression 106 of the outer and inner conduit structures laminates the outer conduit structure to the inner conduit structure.

Following the compression 106, the cover structure is separated 108 from the assembly of the outer conduit structure, stent structure, inner conduit structure and mandrel. The separation 108 may be accomplished by a vacuum fixture or by cutting the cover structure in the longitudinal direction. Also, a cover structure which is formed of silicone material may be unrolled from the outer conduit structure to accomplish the separation 108. Such an unrolling of the cover structure may be initiated by unrolling one end of the cover structure and continuing the unrolling along the length thereof.

After the separation 108, the assembly of the outer conduit structure, stent structure, inner conduit structure is separated 110 from the mandrel. The separation 108 may be accomplished by using a mandrel which has internal passageways which provide a conduit from a compressed air source located externally of the mandrel, and small holes which are located on the outer surface thereof, such as the outer surface 62. The small holes are distributed longitudinally, relative to the mandrel, such that the small holes are contiguous with the grooves, such as the grooves 64. Consequently, the compressed air which is supplied to the internal passageways flows to the small holes and forces the inner conduit structure away from the mandrel in the transverse direction to provide the separation 108.

After the separation 110, the assembly of the outer conduit structure, stent structure, inner conduit structure is heated 112. The heating 112 may provide for maintaining the outer conduit structure, stent structure, and inner conduit structure at a temperature of from 100 degrees F. to 600 degrees F. for a duration of 1 minute to 60 minutes.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. A vascular graft comprising a conduit structure having outer and inner wall surfaces,
    said conduit structure comprising a longitudinal central portion which has an annular cross section and uniform outer and inner diameters, said central portion having a flexibility,
    said conduit structure further comprising a pair of longitudinal intermediate portions each of which has an annular cross section and uniform outer and inner diameters, said outer diameters of said intermediate portions being equal to said outer diameter of said central portion, said central and intermediate portions each being radially compressed such that said radial compression of said intermediate portions is greater than said radial compression of said central portion, said radial compressions of said central and intermediate portions providing for said inner diameter of said central portion to be less than said inner diameters of said intermediate portions, said intermediate portions each being integral with said central portion and located longitudinally such that said central portion is between said intermediate portions, said intermediate portions each having a flexibility which is less than said flexibility of said central portion.

2. A vascular graft according to claim 1, and further comprising a plurality of said central portions located longitudinally such that at least one of said intermediate portions is between a pair of said central portions, each of said central portions having a longitudinal dimension, said longitudinal dimensions of said central portions all being the same.

3. A vascular graft according to claim 1, said intermediate portions each having a longitudinal dimension, said longitudinal dimensions of said intermediate portions all being the same.

4. A vascular graft according to claim 1, wherein said central and intermediate portions each have a density,
    said density of said central portion being less than said density of each of said intermediate portions.

5. A vascular graft according to claim 1, wherein said central and intermediate portions each have a porosity,
    said porosity of said central portion being greater than said porosity of each of said intermediate portions.

6. A vascular graft according to claim 1, wherein said conduit structure comprises PTFE material.

7. A vascular graft according to claim 6, wherein said PTFF material is expanded.

8. A vascular graft according to claim 1, wherein said conduit structure constitutes an inner conduit structure,
    said vascular graft further comprising a stent structure being located in abutting relation to said outer wall surface of said inner conduit structure,
    said vascular graft further comprising an outer conduit structure having outer and inner wall surfaces, said outer conduit structure being in coaxial relation to said inner conduit structure such that said stent and inner conduit structures are within said outer conduit structure, said stent structure being in abutting relation to said inner wall surface of said outer conduit structure, said outer conduit structure being laminated to said inner conduit structure,
    said outer conduit structure comprising a longitudinal central portion having a flexibility,
    said outer conduit structure further comprising a pair of longitudinal intermediate portions each of which are integral with said central portion of said outer conduit structure, said intermediate portions of said outer conduit structure being located longitudinally such that said central portion is between said intermediate portions of said outer conduit structure, said intermediate portions of said outer conduit structure each having a flexibility,
    said central and intermediate portions of said outer conduit structure having the same longitudinal position as said central and intermediate portions of said inner conduit structure, respectively, relative to said vascular graft,
    said flexibility of said central portion of said inner conduit structure and said flexibility of said central portion of said outer conduit structure being greater than said flexibilities of said intermediate portions of said outer conduit structure.

9. A vascular graft according to claim 8, and further comprising a plurality of said central portions of said inner and outer conduit structures, each of said central portions having a longitudinal dimension, said longitudinal dimensions of said central portions all being the same.

10. A vascular graft according to claim 8, wherein said intermediate portions of said inner and outer conduit structures each have a longitudinal dimension, said longitudinal dimensions of said intermediate portions all being the same.

11. A vascular graft according to claim 8, wherein said flexibility of said central portion of said inner conduit structure and said flexibility of said central portion of said outer conduit structure are equal,
    said flexibilities of said intermediate portions of said inner and outer conduit structures being equal.

12. A vascular graft according to claim 8, wherein
    said central and intermediate portions of said outer conduit structure each having a wall thickness defined by a transverse dimension between said outer and inner wall surfaces of said outer conduit structure,
    said central and intermediate portions of said inner and outer conduit structures each having a density,
    said density of said central portion of said inner conduit structure being less than said density of each of said intermediate portions of said inner conduit structure,
    said wall thickness of said central portion of said outer conduit structure being greater than said wall thicknesses of each of said intermediate portions of said outer conduit structure,
    said density of said central portion of said outer conduit structure being less than said densities of each of said intermediate portions of said outer conduit structure.

13. A vascular graft according to claim 8, wherein
said central and intermediate portions of said outer conduit structure each have a wall thickness defined by a transverse dimension between said outer and inner wall surfaces of said outer conduit structure,
said central and intermediate portions of said inner and outer conduit structures each having a porosity,
said porosity of said central portion of said inner conduit structure being greater than said porosity of said intermediate portions of said inner conduit structure,
said wall thickness of said central portion of said outer conduit structure being greater than said wall thicknesses of said intermediate portions of said outer conduit structure,
said porosity of said central portion of said outer conduit structure being greater than said porosities of said intermediate portions of said outer conduit structure.

14. A vascular graft according to claim 8, wherein
said central and intermediate portions of said outer conduit structure each have a cross-section in which said outer wall surface of said outer conduit structure is circular,
said inner and outer conduit structures and stent structure, in combination after said lamination, have a cross-section which is annular.

15. A vascular graft according to claim 8, wherein said inner and outer conduit structures each comprise PTFE material.

16. A vascular graft according to claim 15, wherein said PTFE material is expanded.

17. A method for making a vascular graft comprising:
providing a mandrel including an elongate core structure having an outer surface, said mandrel further including two transverse grooves each of which is formed in the core structure such that the grooves each extend inwardly from the outer surface, the grooves each extending around an entire periphery of the outer surface;
providing a conduit structure having outer and inner wall surfaces, the conduit structure having an inner transverse dimension which is greater than an outer transverse dimension of the core structure;
arranging the conduit structure in coaxial relation to the core structure;
assembling the conduit and core structures such that a longitudinal portion of the inner wall surface of the conduit structure faces the grooves in the core structure;
compressing the conduit structure such that the inner wall surface is forced inwardly into contact with the outer surface of the core structure such that portions of the conduit structure are forced into the grooves and the portion of the conduit structure between the grooves is forced against the outer surface of the core structure;
separating the inner wall surface from the mandrel such that the portions of the conduit structure which were forced into the grooves constitute intermediate portions and the portion of the conduit structure between the intermediate portions constitutes a central portion, the central portion having a transverse wall thickness which is less than a transverse wall thickness of each of the intermediate portions.

18. A method according to claim 17, wherein said step of providing a conduit structure comprises providing a conduit structure formed of PTFE material, said method further comprising
longitudinally expanding the conduit structure before said arranging step, sintering the conduit structure after said longitudinally expanding step and before said arranging step, and
heating the conduit structure after said compressing step.

19. A method according to claim 17, wherein said compressing step comprises applying a gas to the outer wall surface of the conduit structure, the gas having a sufficiently elevated pressure to cause said forcing of the portions of the conduit structure into the grooves and said forcing of the portion of the conduit structure between the grooves against the outer surface of the core structure.

20. A method according to claim 17, and further comprising the step of providing an elongate cover structure having outer and inner wall surfaces and a bore which is bounded transversely the inner wall surface, the cover structure having an inner transverse dimension which is greater than the outer transverse dimension of the conduit structure, the cover structure being formed of silicone material,
said arranging step further comprising arranging the cover structure in coaxial relation to the conduit structure,
said assembling step further comprising assembling the cover and conduit structures such that the inner wall surface of the cover structure faces the outer wall surface of the conduit structure which has the same longitudinal position as the inner wall surface thereof which faces the grooves in the core structure,
said compressing step further comprising compressing the cover structure such that the inner wall surface thereof is forced inwardly into contact with the outer wall surface of the conduit structure to provide said compressing of the conduit structure, said compressing of the conduit structure providing for said forcing of the portions of the conduit structure into the grooves and said forcing of the portion of the conduit structure between the grooves against the outer surface of the core structure,
said separating step further comprising separating the inner wall surface of the cover structure from the outer wall surface of the conduit structure.

21. A method according to claim 17, wherein the conduit structure constitutes an inner conduit structure,
said method further comprising providing a stent structure before said arranging step, the stent structure having an outer transverse dimension,
said method further comprising providing an outer conduit structure before said arranging step, the outer conduit structure having outer and inner wall surfaces, the outer conduit structure having an inner transverse dimension which is greater than an outer transverse dimension of the stent structure,
said arranging step further comprising arranging the stent structure in close or abutting relation to the outer wall surface of the inner conduit structure,
said arranging step further comprising arranging the outer conduit structure in coaxial relation to the inner conduit structure,
said assembling step further comprising assembling the outer and inner conduit structures such that the inner wall surface of the outer conduit structure faces the outer wall surface of the conduit structure and the stent structure is between the inner and outer conduit structures,
said compressing step further comprising compressing the outer conduit structure such that the inner wall surface thereof is forced inwardly into contact with the stent and inner conduit structures to provide said compressing of the inner conduit structure, said compressing of the inner conduit structure providing for said forcing of the portions of the inner conduit structure into the grooves and said forcing of the portion of the inner conduit structure between the grooves against the outer surface of the core structure, said compressing of the outer and inner conduit structures further causing laminating of the outer conduit structure to the inner conduit structure.

* * * * *

UNITED STATES PATENT AND TRADEMARK OFFICE
CERTIFICATE OF CORRECTION

PATENT NO.       : 7,655,035 B2
APPLICATION NO.  : 11/243821
DATED            : February 2, 2010
INVENTOR(S)      : Sowinski et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 298 days.

Signed and Sealed this

Twenty-third Day of November, 2010

David J. Kappos
*Director of the United States Patent and Trademark Office*